US010463265B2

(12) United States Patent
Bierbrauer et al.

(10) Patent No.: US 10,463,265 B2
(45) Date of Patent: Nov. 5, 2019

(54) IMPLANTABLE ELECTRODE ARRAY

(71) Applicant: CorTec GmbH, Freiburg (DE)

(72) Inventors: Tom Colin Bierbrauer, Freiburg (DE);
Joern Rickert, Freiburg (DE);
Christian Henle, Freiburg (DE);
Martin J. Bak, Potomac, MD (US);
Nuri Firat Ince, Humble, TX (US)

(73) Assignee: CorTec GmbH, Freiburg (DE)

( * ) Notice: Subject to any disclaimer, the term of this patent is extended or adjusted under 35 U.S.C. 154(b) by 0 days.

(21) Appl. No.: 15/595,102

(22) Filed: May 15, 2017

(65) Prior Publication Data

US 2017/0245772 A1   Aug. 31, 2017

Related U.S. Application Data

(63) Continuation of application No. PCT/EP2015/076588, filed on Nov. 13, 2015.

(60) Provisional application No. 62/079,215, filed on Nov. 13, 2014.

(51) Int. Cl.
| | |
|---|---|
| *A61B 5/04* | (2006.01) |
| *A61N 1/05* | (2006.01) |
| *A61N 1/04* | (2006.01) |
| *A61B 5/0478* | (2006.01) |
| *A61B 5/00* | (2006.01) |

(52) U.S. Cl.
CPC ........ *A61B 5/04001* (2013.01); *A61B 5/0478* (2013.01); *A61B 5/6868* (2013.01); *A61N 1/0476* (2013.01); *A61N 1/0502* (2013.01); *A61N 1/0531* (2013.01); *A61N 1/0551* (2013.01); *A61B 5/4094* (2013.01); *A61B 2562/125* (2013.01); *A61N 1/0534* (2013.01)

(58) Field of Classification Search
CPC . A61B 5/04001; A61N 1/0502; A61N 1/0476
USPC .......................................... 600/378; 607/116
See application file for complete search history.

(56) References Cited

U.S. PATENT DOCUMENTS

| | | | | |
|---|---|---|---|---|
| 6,044,304 | A * | 3/2000 | Baudino | A61N 1/0539 |
| | | | | 600/378 |
| 8,774,891 | B1 * | 7/2014 | Osa | A61B 5/0478 |
| | | | | 600/378 |
| 9,700,221 | B2 * | 7/2017 | Rajaraman | A61B 5/04001 |
| 2004/0176831 | A1 | 9/2004 | Gliner et al. | |
| 2013/0144365 | A1 | 6/2013 | Kipke et al. | |
| 2015/0289778 | A1 * | 10/2015 | Ohl | A61B 5/0478 |
| | | | | 600/301 |

OTHER PUBLICATIONS

International Search Report with Written Opinion issued for corresponding International Paten Application No. PCT/EP2015/076588 dated May 11, 2016.

* cited by examiner

*Primary Examiner* — Lee S Cohen
(74) *Attorney, Agent, or Firm* — Myers Wolin, LLC

(57) ABSTRACT

An implantable electrode array is provided, the electrode array comprising a substrate, the substrate having a front side and a back side, and a first number of first electrodes. The first electrodes are formed as contact pads, and are arranged on the front side. The substrate comprises a second number of prefabricated holes at predetermined positions, the holes extending from the front side through the substrate towards the back side, and being arranged such the holes may be penetrated by elongated electrodes placed at the predetermined positions.

19 Claims, 5 Drawing Sheets

US 10,463,265 B2

IMPLANTABLE ELECTRODE ARRAY

CROSS REFERENCE TO RELATED APPLICATIONS

This application is a continuation of International Application No. PCT/EP2015/076588, filed Nov. 13, 2015, which claims priority to U.S. Provisional Application No. 62/079,215, filed Nov. 13, 2014, the contents of which are incorporated by reference herein.

FIELD OF THE INVENTION

This application relates to implantable electrode arrays. More specifically, the application relates to implantable electrode arrays comprising a flat substrate, the substrate having a front side and a back side, a first number of first electrodes, the first electrodes being formed as flat contact pads, and being arranged on the front side.

BACKGROUND OF THE INVENTION

Such an electrode array can be used for acute or chronic (i.e., long-time) implantation in humans and/or animals and for recording and/or stimulation, in particular at the cerebral surface of the cortex. Signals recorded with the contact pads of such planar electrodes may be e.g., of the ECoG (Electrocorticography) type.

If, on the other hand, simultaneous recording and/or stimulation in depth of the cortex is additionally required, elongated electrodes (depth electrodes) have to be used which reach into such deeper regions of the cortex. Such elongated electrodes may be placed at the same superficial position of the cortex as the electrode array comprising the planar electrodes. With the small sensing surfaces, the elongate electrodes may be used for recording the activity of single neurons or oscillatory brain activity in the form of local field potentials (LFPs) which represents the activity of a population of neurons in a small volume. The same depth electrodes can also be used for providing micro stimulation to small populations of neurons. Together with planar and elongated contacts, this electrode can simultaneously sense neural activity at various spatial resolutions at the cortical surface and in different layers of the cortex.

Likewise in the peripheral nervous system or the spinal cord, the electrode array is used to record and or stimulate from the surface of the nerve/spinal cord, and the elongated electrodes are used to record/stimulate from within the nerve/spinal cord.

SUMMARY

It is an object of the present invention to provide an implantable electrode array having electrodes being formed as contact pads, which allows for positioning of elongated electrodes at the superficial position of the brain of a human or an animal where the electrode array is implanted, as well a method of producing such an array.

This object is achieved by the electrode arrays of the claims, by the assemblies of the claims, and by the methods of the claims.

Advantageous implementations are defined in the respective dependent claims.

DETAILED DESCRIPTION OF THE PREFERRED EMBODIMENTS

Figure 1:
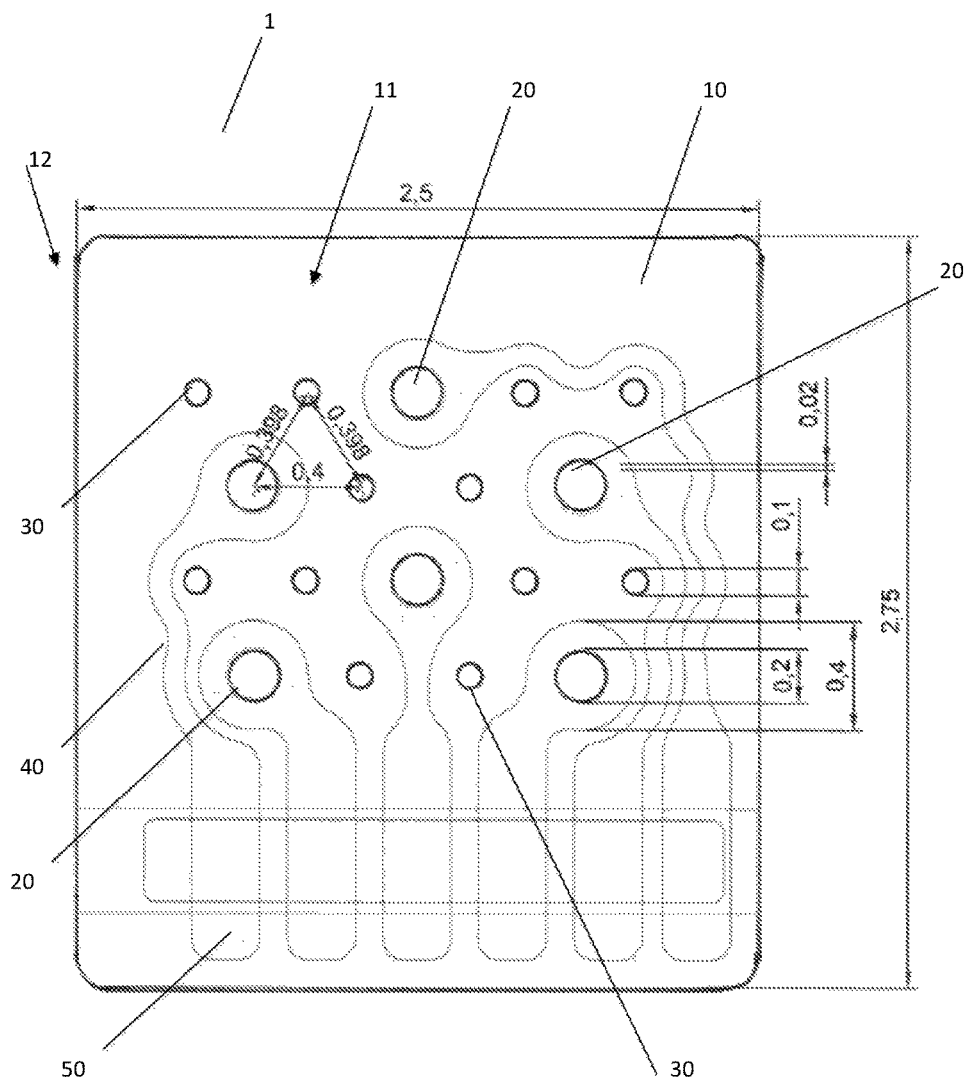
FIG. 1 is a view onto the front side of the electrode array of a first embodiment of the invention.

FIG. 1 is a view onto the implantable electrode array 1 according to a first embodiment of the invention. The implantable electrode array 1 comprises a substrate 10 having a front side 11 and a back side 12, The electrode array 1 further comprises a first number of first electrodes 20, the first electrodes 20 being formed as contact pads, and being arranged on the front side 11 of the substrate 10. The substrate 10 comprises a second number of prefabricated holes 30 at predetermined positions, the holes 30 extending from the front side 11 through the substrate 10 towards the back side 12, and being arranged such the prefabricated holes 30 may be penetrated by elongated electrodes 200 (FIG. 2) passed through the substrate 10 at the predetermined positions.

"Prefabricated" means that the holes 30 are formed in the substrate during production process of the electrode array 1.

"Front side" 11 is the side of the array 1 which faces to the surface of the cortex where the signals are recorded from.

"Back side" 12 is the rearward side of the array 1.

The contact pads are 20 brought in direct contact with the cortex.

The substrate 10 is a flat (foil) substrate, the first electrodes 20 are flat, too. The substrate 10 comprises, or is made of, a flexible material, e.g., silicone, parylene, or polyimide. The implantable electrode array 1 further comprises metal tracks 40 which lead to bond pads 50, which are connected to external wiring and connectors (not illustrated in the figures). Via the external wiring, neural signals recorded by pads 20 are transmitted to external devices, and signals for neural stimulation are transmitted to pads 20.

The prefabricated holes 30 have cross sectional shapes which correspond to the cross sectional shapes of the elongated electrodes 200. In this embodiment, the elongated electrodes 200 have the form of needles, and correspondingly the cross sectional shape of the holes 30 is circular.

In a further embodiment, the prefabricated holes 30 have sizes (diameters) which are smaller than the sizes of the portions of the elongated electrodes which penetrate the prefabricated holes, i.e., their diameters are smaller than the diameters of the elongated electrodes 200.

Then, such prefabricated holes 30 are stretched when the elongated electrodes 200 are inserted from the back side 11 through the holes 30 with their tip portions 220 first. Stretching of the holes 30 by the inserted electrodes has a sealing effect around the hole against liquids.

The elongated electrodes 200 may be better passed through the holes if the electrodes are tapered from their shaft portions 210 to their tip portions 220.

Typical dimensions (in mm) of the elements are given in FIG. 1.

Figure 2:
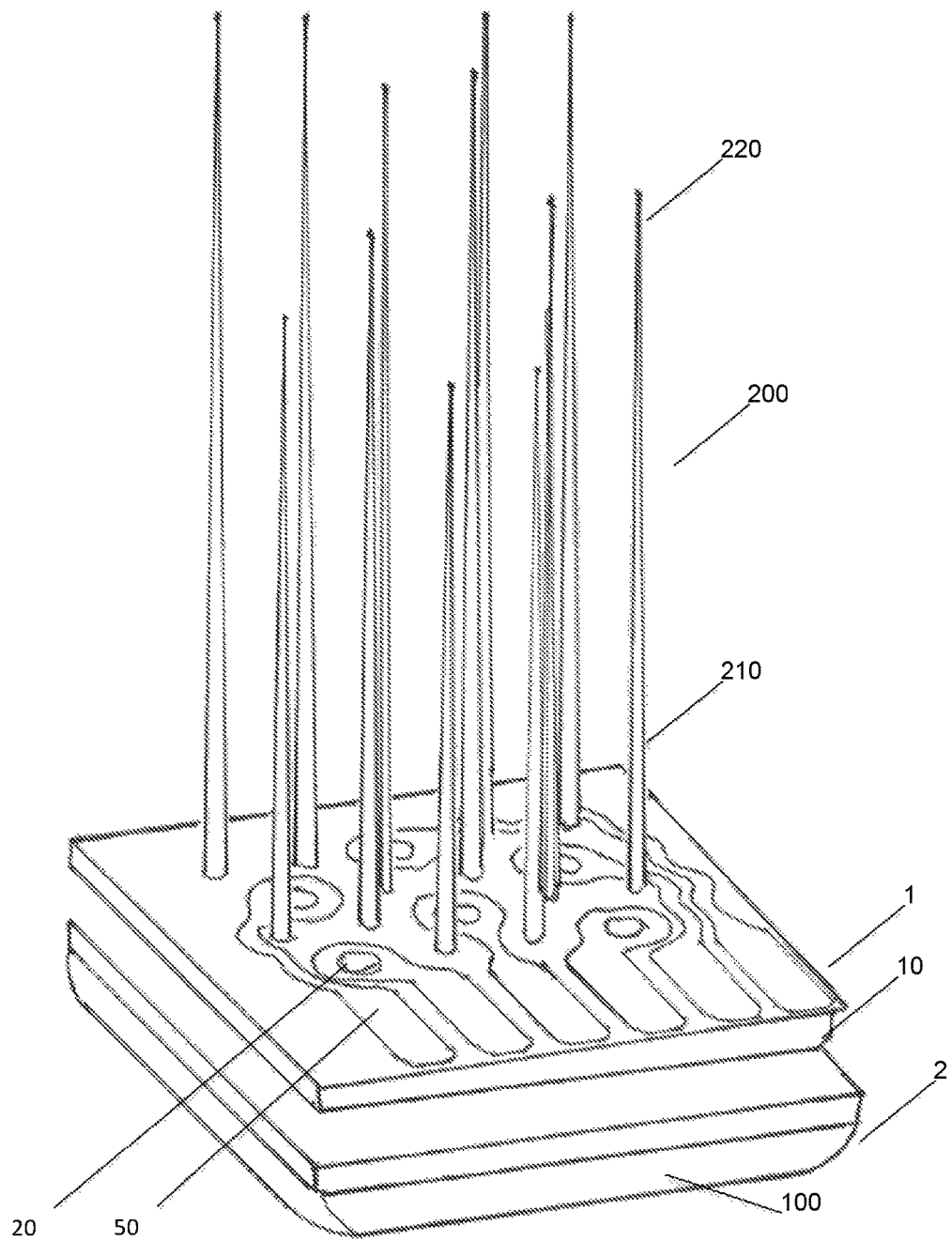
FIG. 2 illustrates the electrode array with elongated electrodes mounted thereon.

FIG. 2 illustrates the electrode array 1 with elongated electrodes 200 passing through it. The elongated electrodes 200 are oriented in a direction perpendicular to the front side 11. As can be seen from the FIG. 2, the elongated electrodes 200 are of the needle type. Each of the needles is tapered from shaft portion 210 to the tip portion 220 thereof. In this embodiment, the needles 200 are fixed with their shaft portions 210 on a second substrate 100, thus forming a second electrode array 2.

The second electrode array 2 may be fabricated such that it comprises elongated electrodes 200 at predetermined positions on the second substrate 100. As an example, the second electrode array 2 may have 18 or 36 elongated electrodes 200 arranged on the second substrate 100. The second substrate 100 is fabricated from a rigid material.

The second substrate 100 mounted on the array 1 is parallel to the array 1. The elongated electrodes 200 are perpendicular to the substrate 10.

When the array 1 and the second array 2 with the elongated electrodes (needles) 200 are inserted into the human being or into the animal, the electrode array 1 is fixed with its back side 11 onto the second substrate 100 of the array 2.

Another option is to assemble the electrode array 1 and the second array 2 prior to inserting the combination intro the brain.

When inserted into the brain, the elongated electrodes 200 should be perpendicular to the brain otherwise damage to the brain may occur during the insertion process.

The elongated electrodes 200 may be rigid needles which maintain their form when being passed through the prefabricated holes 30 of the substrate 10 and being inserted into the destined location in the human or animal body.

In another embodiment, the elongated electrodes 200 are made from a flexible material. Then, an insertion tool is needed for guiding the flexible electrodes 200 through the prefabricated holes array 1 and for inserting the flexible electrodes 200 into the human body. This tool may be a rigid guide wire. The prefabricated holes 30 of the array 1 may have recesses 80 on their circumferences through which the tool (along with the flexible electrodes 200) may be driven in, and the tool drawn back after insertion of the flexible electrodes 200, refer to FIG. 4C).

In a further embodiment, the elongated electrodes 200 have a flat, sword-like form. Such elongated electrodes 200 can also be made from a flexible material.

The prefabricated holes 30 and the first electrodes (pads) 20 can be arranged on the array 1 in many different ways. FIG. 3 illustrates some possible shapes of prefabricated holes and pads of the first electrode array.

In general, the holes 30 are located at predetermined distances from the edge of the substrate 10 such that they are completely surrounded by the substrate 10.

In general, the prefabricated holes 30 may form a grid on the array with predetermined distances.

Further, the prefabricated holes 30 and the contact pads 20 may be arranged in some way alternately on the array 1 with predetermined distances to each other, refer also to FIG. 1 and FIG. 2.

Figure 3A:
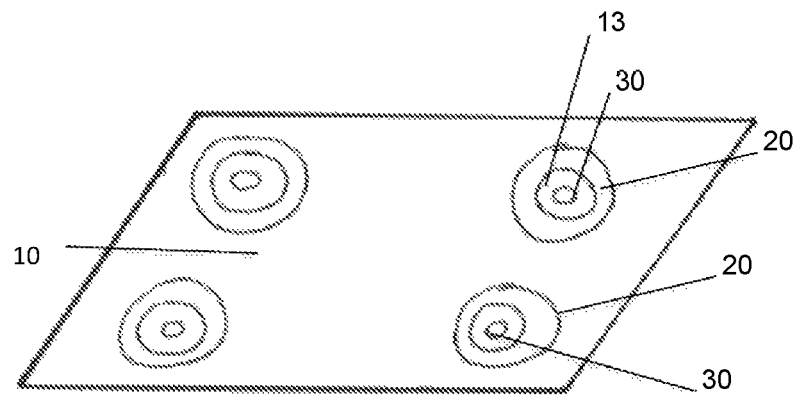
FIGS. 3A-C illustrate the shape of prefabricated holes and pads of the first electrode array.
Figure 3B:
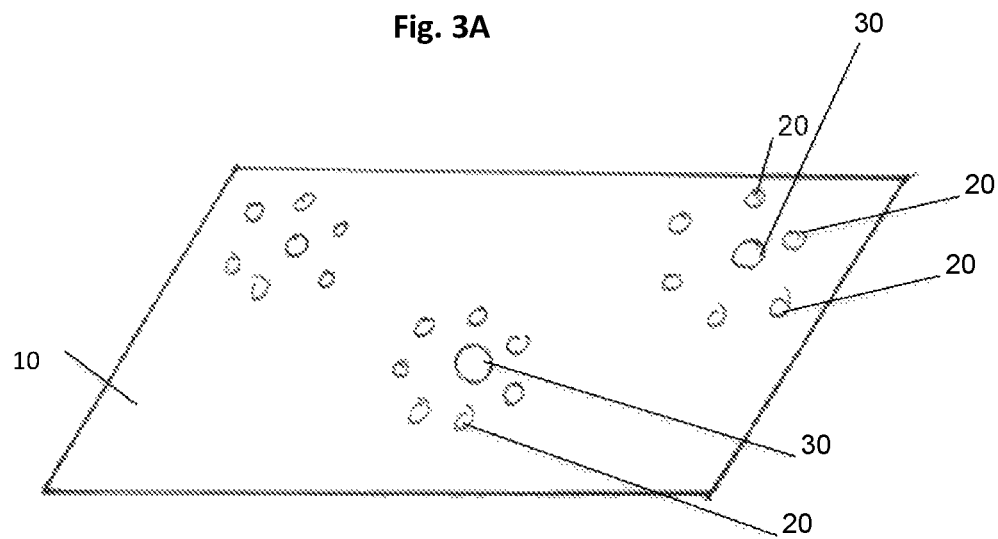

First electrodes 20 may be arranged on a circle around each hole 30 (FIG. 3B).

Figure 5A:
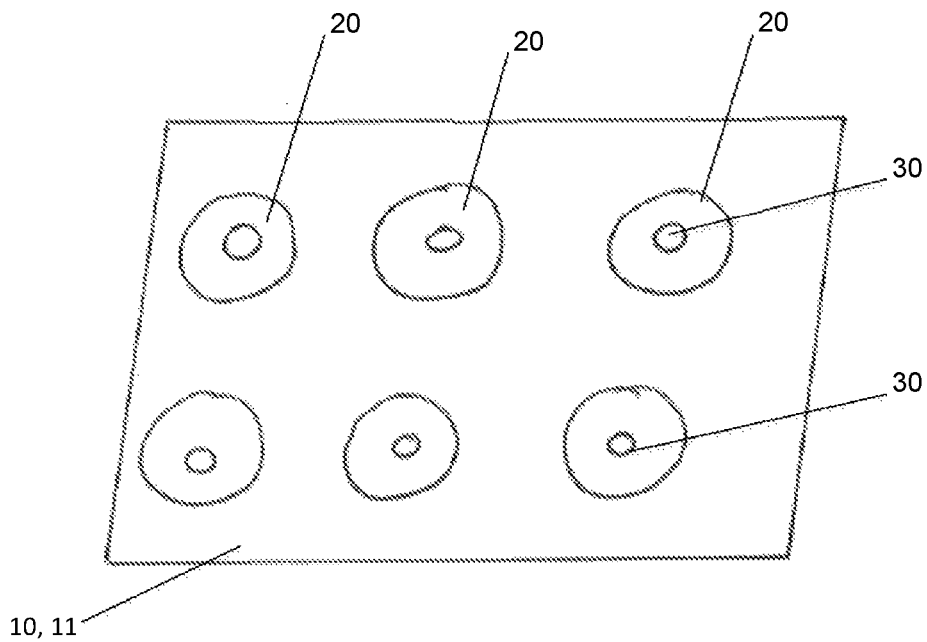
FIGS. 5A-B illustrate annular first electrodes with concentric holes.
Figure 5B:
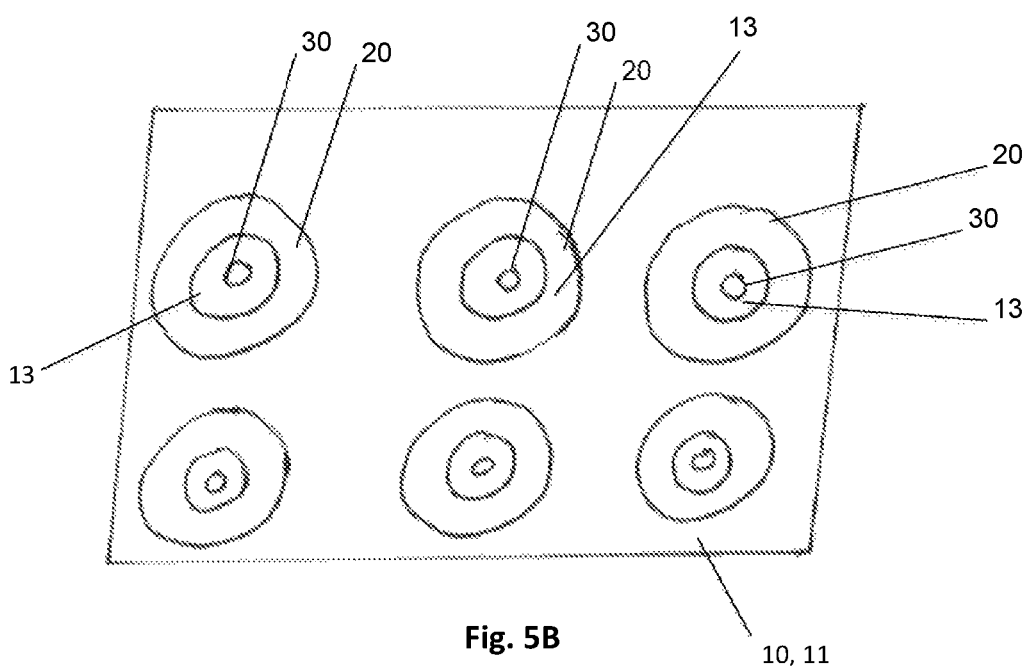

Further, the first electrodes 20 may have annular shape, each first electrode 20 comprising one hole 30 in its center (FIG. 3A, and FIG. 5A-B). Thus, such first electrodes 20 may be formed as a ring having a concentric hole 30. If the elongated electrodes 200 are covered by an insulation, no space between the inner edge of the ring is needed (FIG. 5A), otherwise some space 13 should be left between the inner edge of the ring 20 and the concentric hole 30 (FIG. 5B).

Figure 3C:
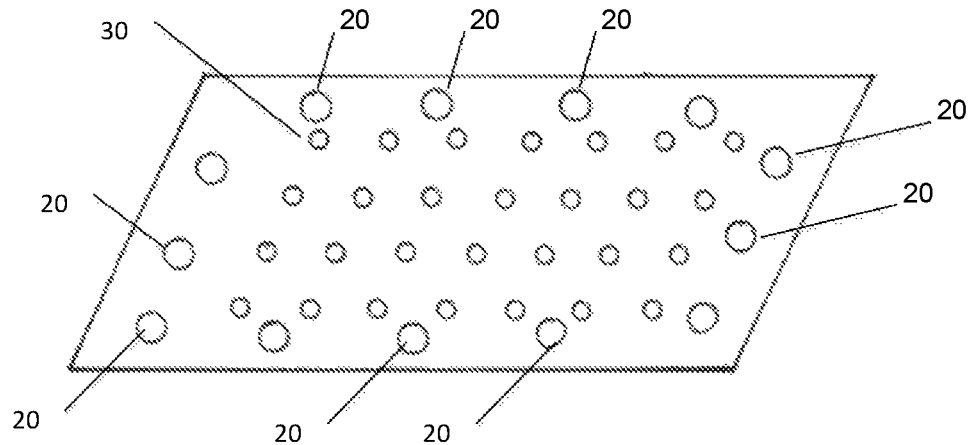

Further, the first electrodes 20 may be arranged such that they surround the complete area where the holes 30 for the elongated electrodes 200 are located (FIG. 3C).

Figure 4A:
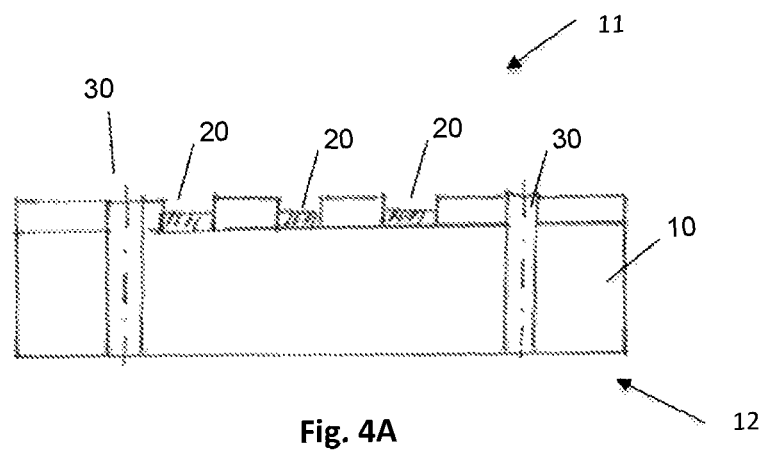
FIGS. 4A-C illustrate forms of the prefabricated holes in the substrate.
Figure 4B:
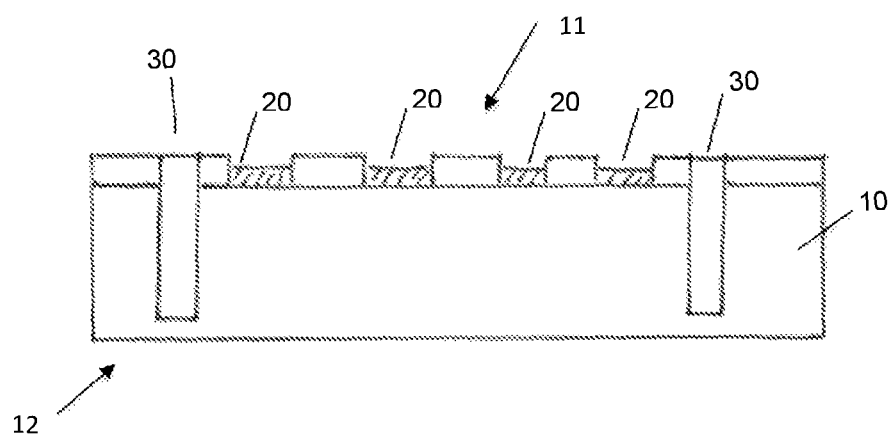
Figure 4C:
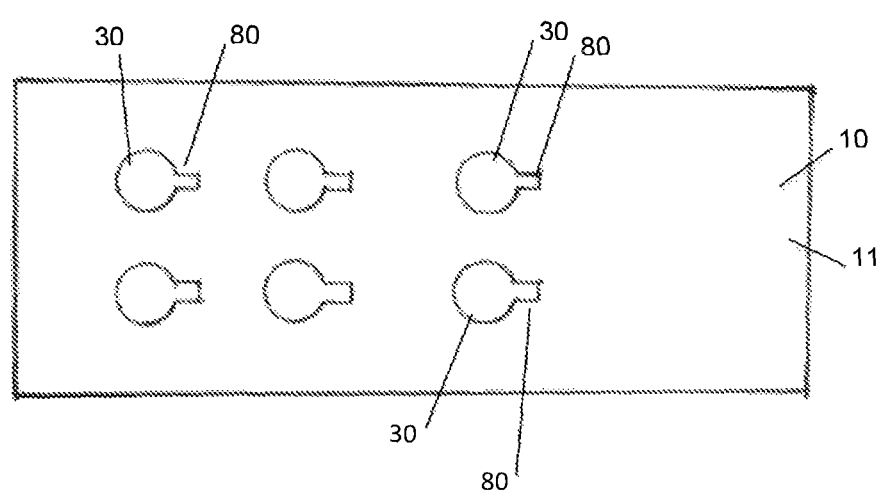

In general, the holes 30 are formed as through holes, traversing the substrate 10 completely (FIG. 4A). In one embodiment, the prefabricated holes 30 do not completely traverse the substrate 10 but are arranged as blind holes (FIG. 4B). Then, only the prefabricated holes 30 which are actually needed are pierced through by the elongate electrodes 200 or by a corresponding tool for guiding the respective elongated electrodes 200 there through.

The electrode array 1 may cover more than one array 2 of elongated needles 200.

The holes 30 are applied to the substrate 10 with a laser beam at the same time when the electrode array 1 is produced. Thus, as soon as the shapes and the positions of the flat electrodes 20 and the elongated electrodes 200 are selected, the electrode array 1 along with the holes 30 is fabricated.

When the electrode array 1 is placed during surgery, the elongated electrodes 200 may be passed through the prefabricated holes 30 to get their final positions.

As mentioned above, the positions of the prefabricated holes 30 correspond to the positions of the elongated electrodes 200 when array 1 and array 2 are assembled together. However, there may be more prefabricated holes 30 on the first array 1 than are actually needed with a particular second array 2 of elongated electrodes 200.

As mentioned above, the shapes of the holes 30 may be adapted to the cross-sectional shapes of the elongated electrodes 200.

For housing needle-type electrodes 200, the shapes of the holes 30 are circular.

For accommodating flat electrodes 200, the shapes of the holes may have the shape of slits.

The material for the first electrodes 20 as well as for the elongated electrodes 200 may be a biocompatible metal, e.g., stainless steel, MP35N, platinum, iridium, tungsten, an alloy thereof, or all other kinds of biocompatible steel-alloys.

The first electrodes 20 may have variable shape, and variable size.

The elongated electrodes 200 may be mounted with their shaft portions 210 in a second substrate 100. The second substrate 100 may be made from ceramics.

The second substrate 200 may be plated with Pt or AgAgCl or another metal over the pads. The second substrate 100 may be 2.5 mm×2.0 mm×0.125 mm but can be in general any size or shape needed. An additional cap made from e.g., ceramic, can be provided on the back side of the second array 2 for protecting the second array 2.

Some embodiments comprise an implantable electrode array assembly, comprising:
a first implantable electrode array 1 as described above;
at least one second electrode array 2,
the at least one second electrode array 2 comprising a second substrate 100, the second substrate 100 having a front side and a rear side, and comprising elongated electrodes 200, the elongated electrodes 200 being arranged on the front side and perpendicular to the front side of the second electrode array 2,
wherein the first substrate 10 comprises prefabricated holes 30 at positions where the number of second electrodes 200 penetrate the first substrate 10 when the first electrode array 1 and the second electrode array 2 are assembled together such that the second electrode array 2 is placed with its front side on the rear side 12 of the first substrate 10.

This is the combination of the electrode array 1 with the contact pads 20 and the elongated electrodes 200 which are fixed on a second substrate 2 and pass through the prefabricated holes 20 of the first substrate 10 of the electrode array 1.

Still further, embodiments may comprise a method of producing an implantable electrode array 1, in particular as described above, comprising:

arranging, on a surface of a first substrate 10, a first number of first electrodes 20, the first electrodes 20 being formed as contact pads, fabricating holes 30, in particular using a laser, in the first substrate 10 at positions where a number of elongated electrodes 200 penetrate the first substrate 10 when arranged on a rear side of the first substrate 10 with respect its surface.

The method may further comprise: arranging the number of elongated electrodes 200 on at least one second substrate 100, and assembling the second substrate 100 comprising the elongated electrodes 200 on the rear side 12 of the first substrate 10 with respect its surface such that the elongated electrodes 200 penetrate the prefabricated holes 30.

The method may still further comprise: forming the holes 30 as blind holes, and piercing through the blind holes 30 upon assembling the second substrate 100 comprising the elongated electrodes 200 onto the first substrate 10.

The method may still further comprise: applying a cover layer, in particular a silicone layer, onto the first substrate with the first electrodes arranged thereon, and removing the layer at the positions of the contact pads 20.

REFERENCE NUMERALS

1 electrode array
2 second electrode array
10 (first) substrate
11 front side
12 back (rear) side
13 space
20 first electrodes, pads
30 prefabricated holes
40 metal tracks
50 bond pads
80 recesses
100 second substrate
200 elongated electrodes
210 shaft portions
220 tip portions

What is claimed is:

1. A method of producing an implantable electrode array assembly, the implantable electrode array assembly, comprising:
    a first implantable electrode array, the first implantable electrode array comprising:
        a first substrate, the first substrate having a front side and a back side,
        a first number of first electrodes, the first electrodes being formed as contact pads, and being arranged on the front side;
    wherein the first substrate comprises a second number of prefabricated holes at predetermined positions,
    the holes extending from the front side through the first substrate towards the back side, and being arranged such the holes may be penetrated by elongated electrodes placed at the predetermined positions, the assembly further comprising;
    at least one second electrode array, the at least one second electrode array comprising:
        a second substrate, the second substrate having a front side and a rear side, and comprising elongated electrodes, the elongated electrodes being arranged on the front side and perpendicular to the front side of the second substrate,
    wherein the prefabricated holes of the first substrate are at positions where the elongated electrodes of the at least one second electrode array penetrate the first substrate when the first electrode array and the second electrode array are assembled together such that the second array is placed with its front side on the back side of the first substrate, and wherein the prefabricated holes have sizes which are smaller than the sizes of the portions of the elongated electrodes which penetrate the prefabricated holes, such that the prefabricated holes are stretched by the penetrating elongated electrodes,
    the method comprising:
        arranging, on the front side of the first substrate, a first number of first electrodes, the first electrodes being formed as contact pads,
        fabricating holes in the first substrate at the predetermined positions where the elongated electrodes penetrate the first substrate when arranged on the back side of the first substrate,
    wherein the holes are applied to the first substrate with a laser beam at the same time when the first electrodes are formed.

2. The method of claim 1, wherein the prefabricated holes have cross sectional shapes which correspond to the cross sectional shapes of the elongated electrodes.

3. The method of claim 1, wherein the prefabricated holes have recesses through which an electrode insertion tool can be passed.

4. The method of claim 1, wherein the first substrate comprises a flexible material.

5. The method of claim 1, wherein the first substrate comprises metal tracks which connect the contact pads with external wiring.

6. The method of claim 1, wherein stretching of the holes has a sealing effect against liquids.

7. The method of claim 1, wherein prefabricated holes are formed as through holes.

8. The method of claim 1, wherein prefabricated holes are formed as blind holes.

9. The method of claim 1, wherein the predetermined positions form a grid.

10. The method of claim 1, wherein the prefabricated holes are surrounded by the first electrodes.

11. The method of claim 1, wherein at least one of the prefabricated holes is surrounded by a first electrode, whereby the first electrode has an annular shape.

12. The method of claim 1, wherein the prefabricated holes and the first electrodes are alternately arranged on the first electrode array.

13. The method of claim 1, wherein each of the elongated electrodes is tapered from a shaft portion to a tip portion.

14. The method of claim 13, wherein each of the elongated electrodes penetrates the hole with its shaft portion.

15. The method of claim 1, wherein the elongated electrodes are of a needle-type.

16. The method of claim 1, wherein the elongated electrodes have flat-shaped portions.

17. The method of claim 1, wherein the elongated electrodes are made from a flexible material.

18. The method of claim 1 further comprising:
    arranging the elongated electrodes on the at least one second substrate, assembling the at least one second substrate comprising the elongated electrodes on the back side of the first substrate such that the elongated electrodes penetrate the prefabricated holes.

19. The method of further comprising:
forming the holes as blind holes, and piercing through the blind holes upon assembling the at least one second substrate comprising the elongated electrodes onto the first substrate.

* * * * *